(12) United States Patent
Kawaki et al.

(10) Patent No.: US 8,558,999 B2
(45) Date of Patent: Oct. 15, 2013

(54) DEFECT INSPECTION APPARATUS AND METHOD UTILIZING MULTIPLE INSPECTION CONDITIONS

(75) Inventors: Koji Kawaki, Hitachinaka (JP); Atsushi Takane, Mito (JP); Hiroshi Kikuchi, Hitachi (JP); Nobuhiro Obara, Hitachinaka (JP); Yuji Inoue, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 62 days.

(21) Appl. No.: 12/078,097

(22) Filed: Mar. 27, 2008

(65) Prior Publication Data
US 2008/0239292 A1    Oct. 2, 2008

(30) Foreign Application Priority Data
Mar. 28, 2007   (JP) .................... 2007-084680

(51) Int. Cl.
*G01N 21/00* (2006.01)
(52) U.S. Cl.
USPC ........................ 356/237.2; 382/263
(58) Field of Classification Search
None
See application file for complete search history.

(56) References Cited

U.S. PATENT DOCUMENTS

| | | | |
|---|---|---|---|
| 5,076,692 A * | 12/1991 | Neukermans et al. | 356/338 |
| 5,903,342 A | 5/1999 | Yatsugake et al. | |
| 6,081,325 A * | 6/2000 | Leslie et al. | 356/237.2 |
| 6,452,677 B1 * | 9/2002 | Do et al. | 356/394 |
| 6,944,325 B2 | 9/2005 | Taguchi et al. | |
| 7,436,508 B2 * | 10/2008 | Wolters et al. | 356/237.5 |
| 2006/0181698 A1 * | 8/2006 | Treves et al. | 356/237.2 |
| 2007/0103676 A1 * | 5/2007 | Marxer et al. | 356/237.3 |

FOREIGN PATENT DOCUMENTS

| | | |
|---|---|---|
| JP | 6-242012 | 9/1994 |
| JP | 9-304289 | 11/1997 |
| JP | 11-51622 | 2/1999 |

OTHER PUBLICATIONS

JP Office Action issued in Japanese Patent Appln. No. JP 2007-084680, dated Jun. 9, 2009 with English translation of JP Office Action.

* cited by examiner

*Primary Examiner* — Gregory J Toatley
*Assistant Examiner* — Rebecca C Bryant
(74) *Attorney, Agent, or Firm* — McDermott Will & Emery LLP

(57) ABSTRACT

To provide a defect inspection apparatus and method adapted to easily assign threshold levels to scattered-light detectors and to appropriately acquire data detected by each scattered-light detector. The apparatus includes a stage device on which to rest a sample; a laser light irradiation device that irradiates the sample on the stage device with inspection light; scattered-light detectors, each of which detects a beam of light, scattered from the sample, and outputs an image signal; a threshold level setter formed so that an associated threshold level for judging whether defects are present is set only for an image signal selected from individual image signals of the scattered-light detectors or from image signals obtained by arithmetic processing based on the image signals, and a threshold level setting circuit that acquires the individual image signals, only if the image signal exceeds the threshold level set in the threshold level setter.

2 Claims, 4 Drawing Sheets

DEFECT INSPECTION APPARATUS AND METHOD UTILIZING MULTIPLE INSPECTION CONDITIONS

BACKGROUND OF THE INVENTION

1. Field of the Invention

The present invention relates to an apparatus and method for inspecting defects, such as foreign substances, flaws, dirt, and other contamination, that are present on a desired surface of a sample such as a semiconductor wafer (hereinafter, referred to simply as a wafer).

2. Description of the Related Art

In recent years, higher-density integration of semiconductor integrated circuit (IC) devices and finer structuring of circuit patterns have progressed. Today, circuit patterns with line widths less than 1 μm are coming to be manufactured. To manufacture these fine-structured ICs at a high yield ratio, it is essential to appropriately manage manufacturing processes by detecting wafer surface defects and inspect the sizes and shapes of the defects or quantitatively examine the degree of cleanliness of various semiconductor-manufacturing apparatuses and processes. At wafer manufacturers and IC-manufacturing factories, therefore, wafer defect inspections with a defect inspection apparatus have traditionally been conducted for appropriate management of the manufacturing processes.

Defect inspection apparatuses of this kind are broadly divided into two types according to inspection scheme. One type is a data comparison type of defect inspection apparatus adapted to compare a bright-field data based on vertical downward illumination, and a previously stored standard pattern. The other type is a defect inspection apparatus that uses such dark-field data as described in, for example, JP-A-11-51622. In the latter type, the light scattered under a dark field of oblique illumination is detected and the existence, position coordinates, and number of defects are recognized from the coordinates of the section estimated as the source of occurrence of the scattered light, or from the intensity of the scattered light.

SUMMARY OF THE INVENTION

The defect inspection apparatus using dark-field data may have a plurality of detectors to detect scattered light. In this case, after being input from the scattered-light detectors to a data processor, detection signals (scattered-light intensity levels) are usually integrated into one detection signal (scattered-light intensity level) by averaging, integral processing, or other arithmetic operations, and then compared with a threshold level to judge whether the data indicates a defect. Accordingly, defect coordinates and the arithmetically obtained detection signal have only been obtainable as inspection results, and detector detection signal data on detected defects has not been acquirable. Although the detection signals acquired by each scattered-light detector can originally be effective data for purposes such as classifying defects according to shape, detection signal acquisition with these scattered-light detectors has traditionally not taken place.

However, even if a defect inspection apparatus with a plurality of scattered-light detectors is constructed to obtain scattered-light intensity information using the scattered-light detectors, an associated threshold level must be assigned to each scattered-light detector in order to suppress the oversizing of the data acquired. It is not easy to optimize the threshold levels to be assigned to individual detectors. If too high a threshold level is assigned, this will result in a lack of the information acquired. Conversely, if too low a threshold level is assigned, this will significantly increase a memory load since the information acquired will include a vast amount of unnecessary information.

The present invention has been made with the above taken into account, and an object of the invention is to provide a defect inspection apparatus and defect inspection method adapted to make it possible to easily assign associated threshold levels to a plurality of scattered-light detectors and to appropriately acquire data detected by each of the scattered-light detectors.

One of major features of the present invention is that the invention comprises: a sample table on which to rest a sample; an inspection light irradiation device that irradiates the sample on the sample table with inspection light; a plurality of scattered-light detectors each constructed to detect the light scattered from the sample and output a detection signal, and; a unit which, on the basis of a predetermined selection parameter, selectively acquires one of the output detection signals of the scattered-light detectors or one of detection signals obtained by arithmetic processing of each detector output detection signal.

Another major feature of the present invention is that in a defect inspection method that uses a sample table on which to rest a sample, a defect inspection apparatus including an inspection light irradiation device for irradiating the sample on the sample table with inspection light, and a plurality of scattered-light detectors each constructed to detect the light scattered from the sample and output a detection signal, one of the output detection signals of the scattered-light detectors or one of detection signals obtained by arithmetic processing of each detector output detection signal is selectively acquired on the basis of a predetermined selection parameter. In addition, some of other further features of the present invention are listed below.

(1) In order to achieve the foregoing object, one aspect of the present invention comprises: a sample table on which to rest a sample, an inspection light irradiation device that irradiates the sample on the sample table with inspection light; a plurality of scattered-light detectors each constructed to detect the light scattered from the sample and output a detection signal; a unit that sets a defect-discriminating threshold level associated with one of the output detection signals of the scattered-light detectors or for one of detection signals obtained by arithmetic processing of each detector output detection signal, and; a unit that acquires each output detection signal of the scattered-light detectors only if the selected detection signal exceeds the associated threshold level.

(2) In above item (1), the present invention preferably further comprises: a unit that sets an associated defect-discriminating threshold level for each output detection signal of the scattered-light detectors or for each detection signal obtained by arithmetic processing of each detector output detection signal, and; means for selecting, as a detection signal acquisition parameter, either a parameter used to acquire each output detection signal of the scattered-light detectors only if the selected detection signal exceeds the associated threshold level, or a parameter which, regardless of whether the selected detection signal exceeds the associated threshold level, is used to acquire each detection signal exceeding the associated threshold level.

(3) In above item (1) or (2), the selected detection signal is preferably any one of the scattered-light detector output detection signals or of the detection signals obtained by arithmetic processing of each detector output detection signal.

(4) In above item (1) or (2), the present invention is preferably adapted so that the selected detection signal is made up of multiple detection signals among all output detection signals of the scattered-light detectors or among all detection signals obtained by arithmetic processing of each detector output detection signal, and so that each output detection signal of the scattered-light detectors is acquired only if all detection signals forming the selected detection signal exceed the associated threshold level.

(5) In above item (1), the present invention preferably further comprises: a unit that sets associated individual defect-discriminating threshold levels for each output detection signal of the scattered-light detectors or for each detection signal obtained by arithmetic processing of each detector output detection signal; and a unit that selects, as a detection signal acquisition parameter, either a parameter used to acquire each output detection signal of the scattered-light detectors only if one selected specific detection signal exceeds the associated threshold level, a parameter used to acquire each output detection signal of the scattered-light detectors only if all selected multiple detection signals exceed the associated threshold level, or a parameter which, regardless of whether the selected detection signal exceeds the associated threshold level, is used to acquire each detection signal exceeding the associated threshold level.

(6) In order to achieve the foregoing object, another aspect of the present invention comprises: a sample table on which to rest a sample; an inspection light irradiation device that irradiates the sample on the sample table with inspection light; a plurality of scattered-light detectors each constructed to detect the light scattered from the sample and output a detection signal; a unit that sets a common defect-discriminating threshold level for detection signals, and; a unit that acquires each output detection signal of the scattered-light detectors only if any one of the scattered-light detector output detection signals or of detection signals obtained by arithmetic processing of each detector output detection signal exceeds the common threshold level.

(7) In order to achieve the foregoing object, the present invention is characterized in that in a defect inspection method that uses a defect inspection apparatus including a sample table on which to rest a sample, an inspection light irradiation device for irradiating the sample on the sample table with inspection light, and a plurality of scattered-light detectors each constructed to detect the light scattered from the sample and output a detection signal, an associated threshold level for discriminating defects is set for one of the output detection signals of the scattered-light detectors or for one of detection signals obtained by arithmetic processing of each detector output detection signal, and in that each output detection signal of the scattered-light detectors is acquired only if a selected detection signal exceeds the associated threshold level.

(8) In order to achieve the foregoing object, the present invention is characterized in that in another defect inspection method that uses a defect inspection apparatus including a sample table on which to rest a sample, an inspection light irradiation device for irradiating the sample on the sample table with inspection light, and a plurality of scattered-light detectors each constructed to detect the light scattered from the sample and output a detection signal: a common threshold level for discriminating defects is set for detection signals, and; output detection signals of the scattered-light detectors are each acquired only if any one of the scattered-light detector output detection signals or of detection signals obtained by arithmetic processing of each detector output detection signal exceeds the common threshold level.

The present invention makes it possible to easily set threshold levels for a plurality of scattered-light detectors and to acquire detected data appropriately from each of the scattered-light detectors.

BRIEF DESCRIPTION OF THE DRAWINGS

Other objects and advantages of the invention will become apparent from the following description of embodiments with reference to the accompanying drawings in which.

DESCRIPTION OF THE PREFERRED EMBODIMENTS

Embodiments of the present invention will be described hereunder using the accompanying drawings. In the following embodiments, descriptions will be made according to the cases using an image signal as an example of a detection signal, an image as an example of data, an image comparison type as an example of a data comparison type, a dark-field image as an example of dark-field data, and an image processor as an example of a data processor, respectively.

First Embodiment

Figure 1:
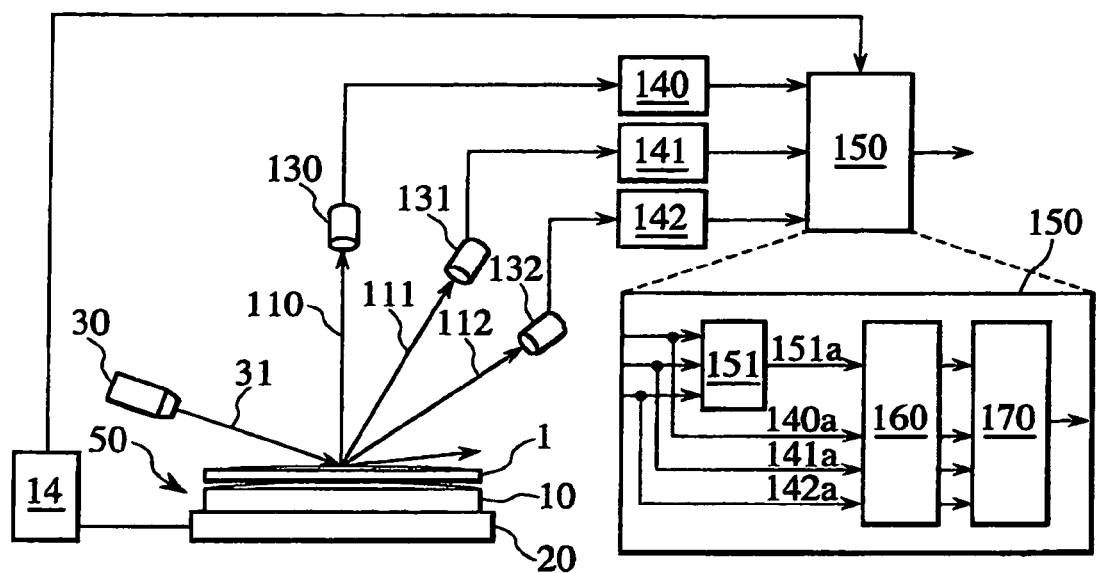
FIG. 1 is a diagram showing a defect inspection apparatus according to a first embodiment of the present invention.

FIG. 1 is a diagram showing a defect inspection apparatus according to a first embodiment of the present invention.

As shown in FIG. 1, the defect inspection apparatus according to the present embodiment detects beams of light, 110 to 112, which are scattered from a wafer sample 1 under a dark field during oblique illumination, and compares intensity of the scattered light with a threshold level to judge whether defects are present. At this time, irradiating position coordinates of laser light (inspection light) 31 that are estimated to be where the scattered beams 110-112 have occurred are determined from position information of a θ-table 10 and an XY table 20, and coordinate information is associated with detected defects. Existence of defects, the coordinate information of the detected defects, and the number of defects are thus recognized. Since the existence of defects on the surface of the wafer 1 results in the wafer being defective, it is significant to acquire surface defect information on the wafer 1 by using such a defect inspection apparatus, partly in terms of examining cleanliness levels of semiconductor-manufacturing apparatuses and processes quantitatively and managing the manufacturing processes appropriately.

(1) Configuration

The defect inspection apparatus shown in FIG. 1 includes a stage device (sample table) 50 on which to rest the wafer 1, a laser irradiation device (inspection light irradiation device) 30 for irradiating the wafer 1 on the stage device 50 obliquely with laser light 31, a plurality of scattered-light detectors 130 to 132 for detecting respectively the beams of light, 110 to 112, scattered from the wafer 1, and output respective image signals (scattered-light intensity levels), and a defect discrimination device 150 that discriminates the existence of defects on the basis of the image signals from the scattered-light detectors 130-132.

(1-1) Stage Device 50

The stage device 50 includes the XY table 20 used to scan the wafer 1 to be inspected, the θ-table 10 that rotates the XY table 20 in a direction of θ, an auto-focusing mechanism (not shown) that moves the XY table 20 in a direction of Z vertically to automatically focus the laser light 31, and a stage controller 14 that controls the constituent elements of the stage device. For total surface inspection of the wafer 1, the surface of the wafer is scanned with the laser light 31 by moving the XY table 20 in XY directions as appropriate during the rotation of the θ-table 10. During scanning with the laser light 31, position information of the θ-table 10 and the XY table 20 is output from the stage controller 14 to the defect discrimination device 150 as coordinate information of a beam spot of the laser light 31 on the wafer 1 (i.e., as coordinate information of a position at which the scattered beams 110-112 have occurred).

(1-2) Laser Irradiation Device 30

The laser irradiation device 30 is positioned diagonally above the wafer 1 on the stage device 50, and serves with a condensing lens (not shown) to constitute an optical system for irradiation. Laser light 31 that has been emitted diagonally from the laser irradiation device 30 towards the wafer 1 is condensed by the condensing lens, and the wafer 1 rested on the stage device 50 is irradiated with the laser light 31 at a small angle.

(1-3) Scattered-Light Detectors 130-132

The scattered-light detectors 130-132 are positioned above the wafer 1 on the stage device 50, and as the laser light 31 is irradiated obliquely onto the surface of the wafer 1, the scattered-light detectors condense the scattered beams 110-112 that are generated as a result of random reflection from the surface of the wafer 1. That is to say, the scattered-light detectors 130-132 are constructed to detect the scattered beams 110-112, respectively, under a dark field.

The scattered beams 110-112 that have been detected by the scattered-light detectors 130-132 are input to respective A/D converters 140 to 142, then digitized by conversion from analog signal form into digital signal form, and output as image signals (scattered-light intensity levels) 140a to 142a.

While an example of providing three scattered-light detectors, 130-132, in the present embodiment is shown, necessary conditions hold if multiple, that is, at least two scattered-light detectors are provided. Briefly, the number of scattered-light detectors can be two or more than three.

(1-4) Defect Discrimination Device 150

As shown in partly enlarged view in FIG. 1, the defect discrimination device 150 has an arithmetic processing circuit 151 that arithmetically processes the image signals 140a-142a, a threshold level setting circuit 160 that sets threshold levels, and a defect discrimination circuit 170 that judges whether defects are present.

(1-4.1) Arithmetic Processing Circuit 151

The arithmetic processing circuit 151 receives the image signals 140a-142a input from the scattered-light detectors 130-132, and then arithmetically operates on one image signal 151a by executing required arithmetic processing (such as averaging or integral processing) based on each of the image signals 140a-142a.

(1-4.2) Threshold Level Setting Circuit 160

The threshold level setting circuit 160 functions as a unit that sets an associated defect existence discrimination threshold level for a selected image signal (hereinafter, referred to as the selected signal) of the image signals 140a-142a from the scattered-light detectors 130-132 or of the three image signals 151a obtained by arithmetic operations based on the image signals 140a-142a. The threshold level setting circuit 160 further functions as a unit that acquires each image signal 130a-132a of the scattered-light detectors 130-132 or the image signal 151a only if the selected signal exceeds the associated threshold level.

Figure 2:
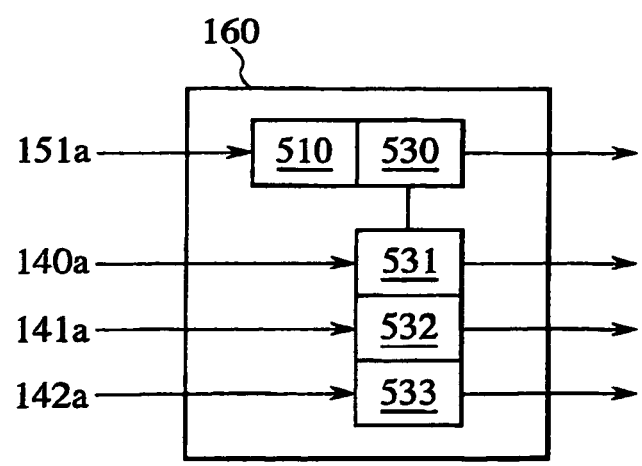
FIG. 2 is a block diagram that shows details of a threshold level setting circuit provided in the defect inspection apparatus according to the first embodiment of the present invention.

FIG. 2 is a block diagram that shows details of the threshold level setting circuit 160.

As shown in FIG. 2, the threshold level setting circuit 160 includes a threshold level setter 530-533 that sets the associated defect existence discrimination threshold level for the image signal 151a based on arithmetic processing by the arithmetic processing circuit 151, or for the image signals 140a-142a of the scattered-light detectors 130-132, and a signal acquisition parameter selector 510 that selects an image signal acquisition parameter.

The image signal 151a output from the arithmetic processing circuit 151 in the present embodiment is input to the threshold level setter 530 via the signal acquisition parameter selector 510. In addition, the image signals 140a-142a that have been detected by the scattered-light detectors 130-132 are input to the threshold level setters 531-533, respectively.

Depending on a setting state of the signal acquisition parameter selector 510, the threshold level setting circuit 160 selects one of the following two parameters, that is, (A1) or (B1), as the image signal acquisition parameter:

(A1) All image signals 140a-142a of the scattered-light detectors 130-132 are acquired, only if the selected signal (in the present example, the image signal 151a) exceeds the associated threshold level.

(B1) Of all image signals 151a and 140a-142a, only those exceeding the associated threshold level are acquired, irrespective of whether the selected signal exceeds the threshold level.

For example, if the setting state of the signal acquisition parameter selector 510 is ON, an image signal is acquired in accordance with parameter (A1), and if the setting state is OFF, an image signal is acquired in accordance with parameter (B1).

ON/OFF selection of the signal acquisition parameter selector 510 is based on an operating signal input from an operating screen or operating input device not shown, to the signal acquisition parameter selector 510. In addition, threshold level setting by the threshold level setters 530-533 is based on respective operating signals input from an operating screen or operating input device not shown, to the threshold level setters 530-533.

(1-4.3) Defect Discrimination Circuit 170

The defect discrimination circuit 170 assigns association between a defect signal that is input, for example, from the threshold level setting circuit 160 (i.e., an image signal exceeding the associated threshold level), and detection coordinate information of a defect signal which is input from the stage controller 14. The defect discrimination circuit 170 also operates on a differential between the defect signal input from the threshold level setting circuit 160, and the associated threshold level. These two kinds of information are output, together with respective source image signals, for example, an external apparatus such as a personal computer (PC) or review apparatus, and are used to manage positions (coordinates), sizes, and quantities of defects, to classify and analyze shapes, kinds, and other attributes of the defects, to quantitatively confirm the cleanliness levels of the semiconductor-manufacturing apparatuses and processes, and hence to manage the manufacturing processes.

(2) Defect Inspection Sequence

A defect inspection sequence in the present embodiment is described below.

When defect inspection is started, first the θ-table 10 rotates under an instruction from the stage controller 14 and the laser light irradiation device 30 irradiates the wafer 1 with laser light 31 at a small angle. After this, the XY table 20 moves in the XY directions under another instruction from the stage controller 14 and the wafer 1 is scanned with the laser light 31.

After the irradiation of the wafer 1 with the laser light 31, dark-field scattered beams of light, 110 to 112, stem from surface defects or circuit patterns (if the circuit patterns are already formed) on the wafer 1. The scattered beams 110-112 are input to the scattered-light detectors 130-132, respectively, and condensed.

The scattered beams that have been detected by the scattered-light detectors 130-132 are input to the respective A/D converters 140-142 arranged at a posterior stage, and are output to the defect discrimination device 150 as digitized image signals (scattered-light intensity levels) 140a-142a.

The image signals 140a-142a that have been input to the defect discrimination device 150 are next input to the arithmetic processing circuit 151. The arithmetic processing circuit 151 executes required arithmetic processing to operate on an image signal 151a based on the image signals 140a-142a. The image signal 151a that has been computed by the arithmetic processing circuit 151 is input to the threshold level setting circuit 160 together with the image signals 140a-142a of the scattered-light detectors 130-132. More specifically, the image signal 151a is input to the threshold level setter 530 via the signal acquisition parameter selector 510, and the image signals 140a-142a are input to the threshold level setters 531-533, respectively.

Figure 3:
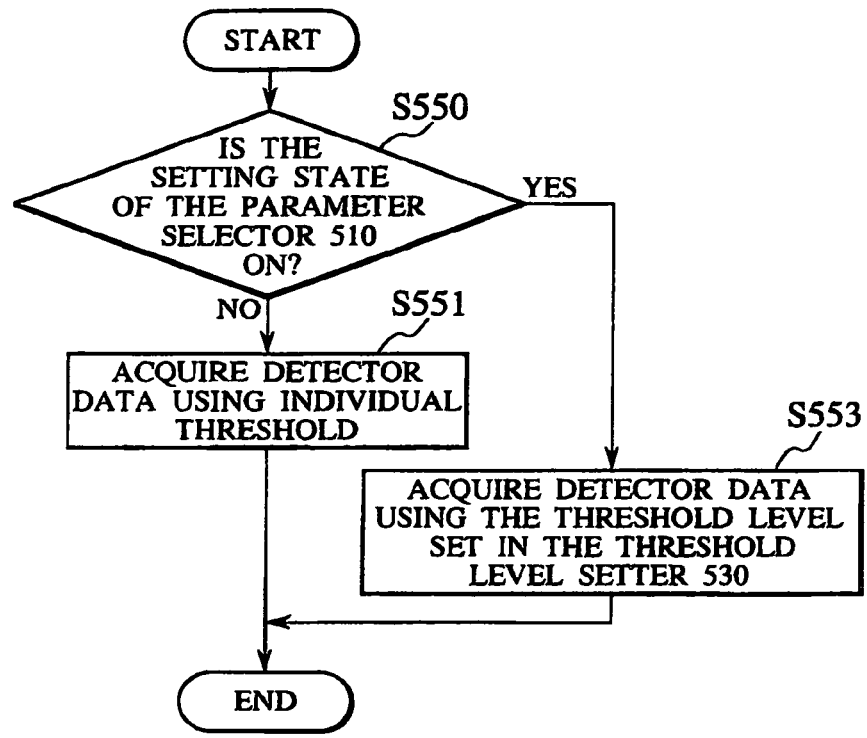
FIG. 3 is a flowchart of a processing sequence by the threshold level setting circuit provided in the defect inspection apparatus according to the first embodiment of the present invention.
Figure 5:
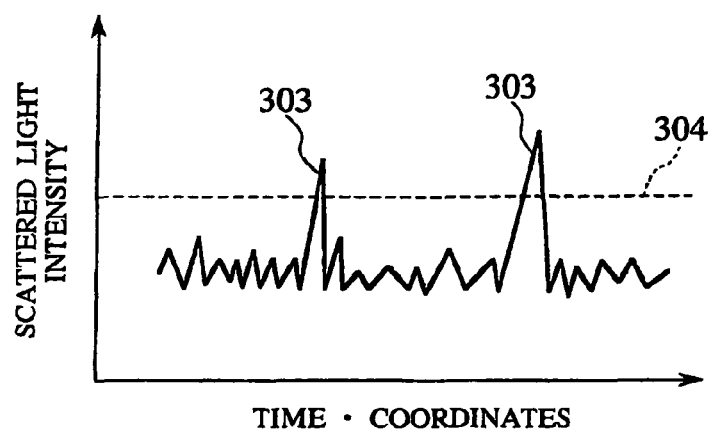
FIG. 5 is a diagram representing a relationship between image signal (scattered-light intensity level) and a threshold level.

FIG. 3 is a flowchart representing a sequence of processing by the threshold level setting circuit 160. As shown in FIG. 5, the threshold level setting circuit 160 first confirms in step S550 whether the setting of the signal acquisition parameter selector 510 is ON. If the setting of the signal acquisition parameter selector 510 is OFF, sequence control is transferred to step S551, and if the setting is ON, sequence control is transferred to step S553.

After the OFF setting of the signal acquisition parameter selector 510 has been confirmed and sequence control transferred to step S551, the threshold level setting circuit 160 acquires image signals in accordance with parameter (B1) described above. Image signals 151a from the arithmetic processing circuit 151 and 140a-142a (raw data signals) from the scattered-light detectors 130-132 within the associated threshold levels that have been set in the respective threshold level setters 530-533 are filtered and only image signals exceeding the threshold levels are output to the defect discrimination circuit 170.

However, after the ON setting of the signal acquisition parameter selector 510 has been confirmed, if sequence control is transferred to step S553, the threshold level setting circuit 160 acquires image signals in accordance with parameter (A1) described above. Thus, the image signal 151a from the arithmetic processing circuit 151 and the image signals 140a-142a (raw data signals) from the scattered-light detectors 130-132 that have been used to calculate the image signal 151a are output to the defect discrimination circuit 170, only if the image signal 151a exceeds the associated threshold level that has been set in the threshold level setter 530. If the image signal 151a does not exceed the threshold level of the threshold level setter 530, the image signals 151a and 140a-142a are all filtered.

After executing steps S551 and S553, the threshold level setting circuit 160 ends the sequence shown in FIG. 3. The threshold level setting circuit 160 repeatedly executes the successive steps during defect inspection.

(3) Comparative Example

Figure 4:
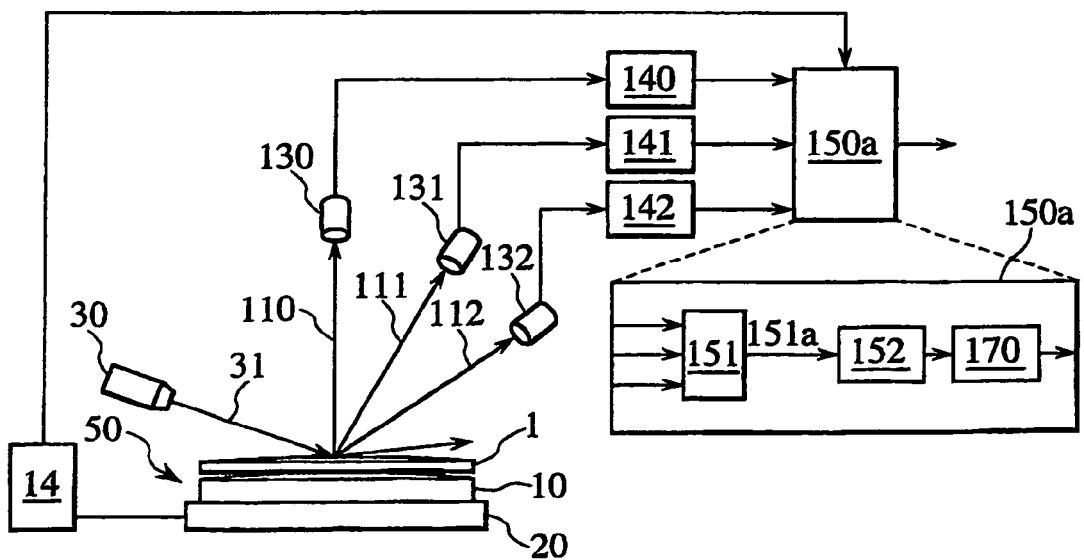
FIG. 4 is a diagram showing a defect inspection apparatus according to a comparative example.

FIG. 4 is a diagram showing a comparative example with respect to the defect inspection apparatus of the present embodiment.

A configuration of a defect discrimination device 150a in the comparative example of FIG. 4 differs from the configuration of the defect discrimination device 150 according to the present embodiment. More specifically, the threshold level setting circuit 160 is omitted. Instead, a threshold level setter 152 is provided that performs substantially the same function as that of the threshold level setter 530.

The threshold level setter 152 receives only the image signal 151a that has been computed by the arithmetic processing circuit 151, and unlike the threshold level setting circuit 160, does not receive the image signals 140a-142a from the scattered-light detectors 130-132. Therefore, the image signal 151a is merely compared with the threshold level set in the threshold level setter 152, and image signals 151a exceeding the threshold level (i.e., defect signals) are output to the defect discrimination circuit 170.

FIG. 5 is a diagram representing a relationship between image signal (scattered-light intensity level) and a threshold level.

As shown in FIG. 5, in this kind of defect inspection apparatus, an image signal (scattered-light intensity level) that has been detected by a scattered-light detector is compared with a threshold level 304 and it is judged that a defect is most likely to be present at a position on the wafer where the scattered light causing the image signal (defect signal 303) exceeding the threshold level 304 has occurred. However, if, as in the comparative example, the plurality of scattered-light detectors 130-132 are used, when one image signal 151a that has been calculated by required arithmetic processing based on image signals 140a-142a from the scattered-light detectors 130-132 is merely compared with the threshold level 304, the information obtained by the defect discrimination circuit 170 at a posterior stage will, even after detection of the defect signal 303, be only the size and coordinates of the defect identified by the defect signal 303, and the intensity levels of the scattered beams detected by the scattered-light detectors 130-132 cannot be discriminated.

Figure 6A:
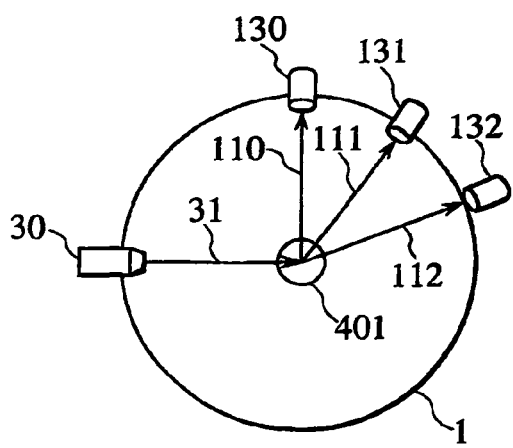
FIGS. 6A and 6B are diagrams explaining a difference in scattered-light occurrence pattern due to a shape of a defect.
Figure 6B:
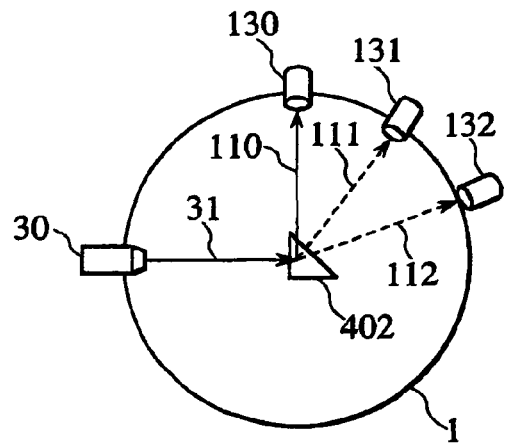

FIGS. 6A and 6B are diagrams explaining a difference in scattered-light occurrence pattern due to a shape of the defect, and the diagrams are equivalent to top views of the wafer 1 existing during defect inspection.

If foreign substances 401 and 402 are sticking to the surface of the wafer 1, when the wafer is irradiated with the laser light 31 from the laser light irradiation device 30, scattered beams 110-112 from the foreign substances 401, 402 are detected by the scattered-light detectors 130-132, respectively. However, not all of the scattered beams 110-112 are uniform in scattering direction; the way the intensity of the scattered beams 110-112 varies from direction to direction differs according to the particular shape of the foreign substance 401, 402.

In other words, as shown in FIG. 6A, the foreign substance 401 may be nearly spherical and the scattered beams 110-112 that are input to the scattered-light detectors 130-132 may be almost uniform, whereas the shape of the defect, as with that of the foreign substance 402 shown in FIG. 6B, may completely differ from a spherical shape and be triangular, for example. In addition, the scattered beam 110, for example, that is input to the scattered-light detector 130 may be strong and the scattered beams 111, 112 that are input to the scattered-light detectors 131, 132 may be weak, compared with the scattered beam 110.

In the comparative example, the image signals 140a-142a from the scattered-light detectors 130-132 are not acquired and one image signal 151a formed by integrating the image signals 140a-142a is detected as the defect signal, so the amount of information for analyzing the shape of the defect is not always sufficient.

In the comparative example, however, to acquire the image signals 140a-142a of the scattered-light detectors 130-132 along with the one image signal 151a, the associated independent threshold levels must be set in the scattered-light detectors 130-132 in order to suppress the oversizing of the information acquired. It is not easily to optimize each threshold level for the image signals 140a-142a of the scattered-light detectors 130-132. Too high a threshold level results in a lack of the information acquired, and too low a threshold level significantly increases a memory load since the information acquired will include unnecessary information.

(4) Effects of the Embodiment of the Invention

In the present embodiment, during image signal acquisition in accordance with parameter (A1), the image signals 151a and 140a-142a are acquired when a defect signal is detected as a result of comparison between the image signal 151a and the threshold level thereof. Since the image signals 140a-142a from the scattered-light detectors 130-132 relating to the defect signal are acquired, the amount of information acquired increases, which is informative for purposes such as classifying and analyzing the shapes of defects, in addition to confirming the coordinates, sizes, and number of defects.

At this time, for image signal acquisition in accordance with parameter (A1) in the present embodiment, the threshold levels of the image signals 140a-142a from the scattered-light detectors 130-132 have no relationship with respect to the amount of information acquired. The threshold levels can therefore be set more easily than for the acquisition of the image signals 140a-142a in the comparative example.

In addition, under parameter (A1), provided that the image signal 151a stays within the associated threshold level, none of the image signals 151a, 140a-142a is output to the defect discrimination circuit 170 provided at the posterior stage. This is also beneficial for exclusively acquiring only a plenty of necessary information on defect signals and minimizing the amount of other information acquired. It is thus possible to reduce likelihood of the oversizing of the data acquired, as in the acquisition of the image signals 140a-142a in the comparative example of FIG. 4, and hence to acquire the image signals 140a-142a from the scattered-light detectors 130-132 appropriately. This, in turn, makes it possible to suppress an increase in the amount of data due to the acquisition of the image signals 140a-142a, and is further effective for realizing high throughput in the defect discrimination circuit 170 provided at the posterior stage.

Additionally, since the image signal acquisition parameter is selectable between (A1) and (B1) in the present embodiment, the independent threshold levels set for each image signal 140a-142a of the scattered-light detectors 130-132, not the single threshold level set in the threshold level setter 530, can be used to easily acquire image signals.

An example of selecting one image signal 151a from the image signals 140a-142a of the scattered-light detectors 130-132 or from image signals 151a formed by arithmetic processing based on the image signals 140a-142a and acquiring image signals in accordance with parameter (A1) has been taken in the present embodiment. However, any one of the other image signals 140a-142a may be selected.

Second Embodiment

The above first embodiment has been described taking an example of selecting one image signal from the image signals 140a-142a of the scattered-light detectors 130-132 or from the image signals 151a formed by arithmetic processing based on the image signals 140a-142a. However, two to all of the image signals 151a, 140a-142a may be selected. In this case, all of the image signals 151a, 140a-142a may be acquired only if the selected signals all exceed the respective threshold levels, or all of the image signals 151a, 140a-142a are likely to be acquired only if at least one of the selected signals exceeds the associated threshold level.

An example of acquiring all image signals 151a, 140a-142a only if the selected plurality of signals all exceed the respective threshold levels is shown in the present embodiment.

Figure 7:
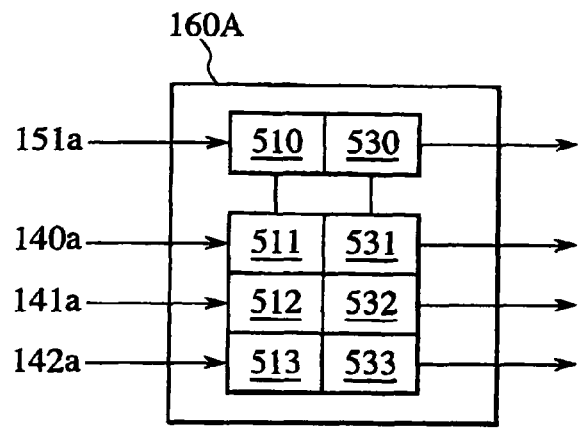
FIG. 7 is a block diagram that shows details of a threshold level setting circuit provided in a defect inspection apparatus according to a second embodiment of the present invention.

FIG. 7 is a block diagram that shows details of a threshold level setting circuit equipped in the defect inspection apparatus according to a second embodiment of the present invention. As shown in FIG. 7, the threshold level setting circuit 160A in the present embodiment has signal acquisition parameter selectors 511 to 513 not only in the threshold level setter 530 for the image signal 151a, but also in the threshold level setters 531 to 533 of the scattered-light detectors 130 to 132. In the present embodiment, the image signals 151a, 140a-142a are respectively input to the associated threshold level setters 530-533 via the signal acquisition parameter selectors 510-513. In addition, a setting change (ON/OFF selection) of each signal acquisition parameter selector 511-513 is also conducted according to a level of the operating signal input from an operating screen or operating input device not shown, to the signal acquisition parameter selector 510. Other configurational aspects of the present embodiment are substantially the same as those of the first embodiment, and operation other than processing within the threshold level setting circuit 160A is also substantially the same as in the first embodiment.

Depending on the setting state of the signal acquisition parameter selector 510-513, the threshold level setting circuit 160A selects one of the following three image signal acquisition parameters, that is, (A2), (B2), or (C2):

(A2) All image signals 140a-142a of the scattered-light detectors 130-132 are acquired, only if a selected specific (representative) signal (in the present example, the image signal 151a) exceeds the associated threshold level.

(B2) Of all image signals 151a and 140a-142a, only those exceeding the associated respective threshold levels are acquired, irrespective of whether selected signals (in the present example, the image signals 151a, 140a) exceeds the threshold level.

(C2) All image signals 140a-142a of the scattered-light detectors 130-132 are acquired, only if selected signals (in the present example, the image signals 151a, 140a) both exceed the respective threshold levels.

That is to say, if the setting state of the signal acquisition parameter selector 510 which turns ON/OFF the function of the threshold level setter 530 for the image signal 151*a* (selected representative signal) is ON and the setting state of the signal acquisition parameter selector 511 which turns ON/OFF the function of the threshold level setter 531 for the image signal 140*a* (another selected signal) is OFF, an image signal is acquired in accordance with parameter (A2). If the settings of the signal acquisition parameter selectors 510, 511 are both OFF, an image signal is acquired in accordance with parameter (B2). If the settings of the signal acquisition parameter selectors 510, 511 are both ON, an image signal is acquired in accordance with parameter (C2).

A defect inspection sequence in the present embodiment is described below.

Figure 8:
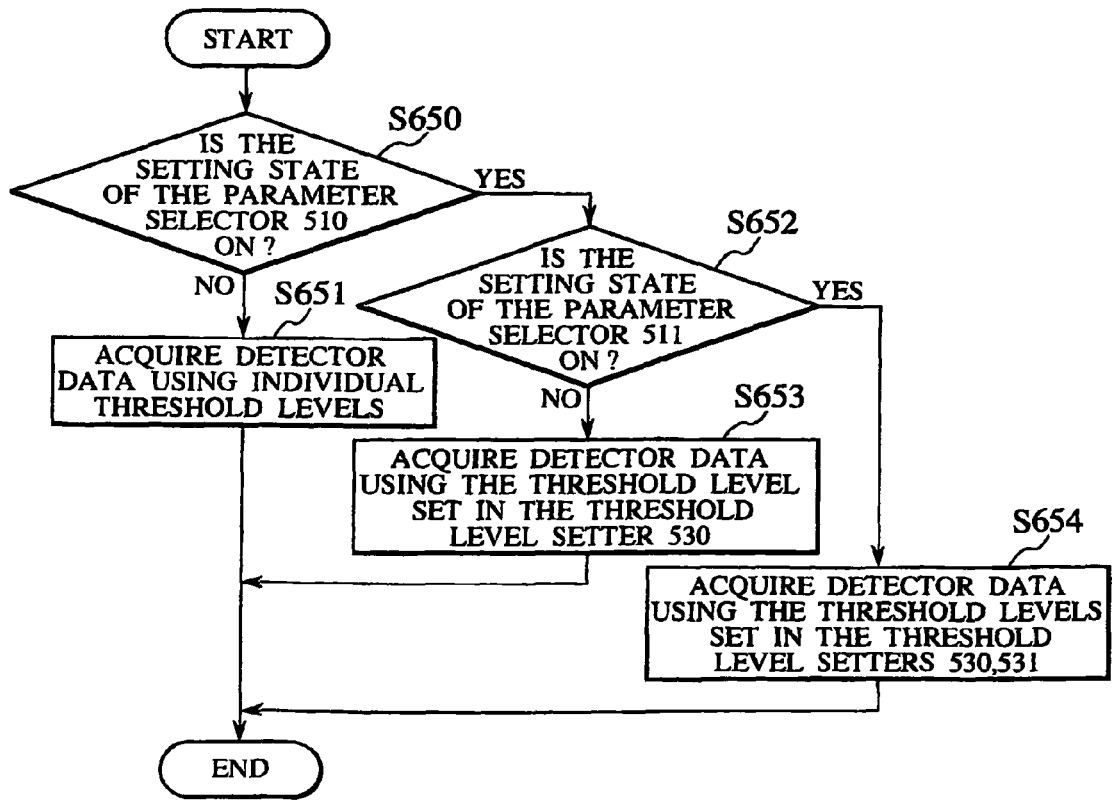
FIG. 8 is a flowchart of a processing sequence by the threshold level setting circuit provided in the defect inspection apparatus according to the second embodiment of the present invention.

FIG. 8 is a flowchart showing a processing sequence of the threshold level setting circuit 160A.

As shown in FIG. 8, the threshold level setting circuit 160A first confirms in step S650 whether the setting state of the signal acquisition parameter selector 510 for the image signal 151*a* (selected representative signal) is ON. Sequence control is transferred to step S651 if the setting of the signal acquisition parameter selector 510 is OFF, or to step S652 if the setting is ON.

After the OFF setting of the signal acquisition parameter selector 510 has been confirmed and sequence control transferred to step S651, the threshold level setting circuit 160A acquires image signals in accordance with parameter (B2) described above. Thus, of all image signals 151*a* from the arithmetic processing circuit 151 and 140*a*-142*a* (raw data signals) from the scattered-light detectors 130-132, only those within the associated independent threshold levels that have been set in each associated threshold level setter 530-533 are filtered and images signals exceeding the threshold levels are output to the defect discrimination circuit 170. Processing in step S651 is equivalent to that of step S551 in the first embodiment.

However, after the ON setting of the signal acquisition parameter selector 510 has been confirmed, if sequence control is transferred to step S652, the threshold level setting circuit 160A confirms whether the setting state of the signal acquisition parameter selector 511 for the image signal 140*a* (another selected signal) is ON. Sequence control is transferred to step S653 if the setting of the signal acquisition parameter selector 511 is OFF, or to step S654 if the setting is ON.

After the OFF setting of the signal acquisition parameter selector 511 has been confirmed, if sequence control is transferred to step S653, the threshold level setting circuit 160A acquires image signals in accordance with parameter (A2) described above. Thus, the image signal 151*a* from the arithmetic processing circuit 151 and the image signals 140*a*-142*a* (raw data signals) from the scattered-light detector 130-132 that were used to calculate the image signal 151*a* are output to the defect discrimination circuit 170, only if the image signal 151*a* exceeds the setting of the associated threshold level in the threshold level setter 530. All image signals 151*a*, 140*a*-142*a* are filtered if the image signal 151*a* does not exceed the threshold level within the threshold level setter 530. Processing in step S653 is equivalent to that of step S553 in the first embodiment.

After the ON setting of the signal acquisition parameter selector 511 has been confirmed, if sequence control is transferred to step S654, the threshold level setting circuit 160A acquires image signals in accordance with parameter (C2) described above. Thus, the image signal 151*a* from the arithmetic processing circuit 151 and the image signals 140*a*-142*a* (raw data signals) from the scattered-light detector 130-132 that were used to calculate the image signal 151*a* are output to the defect discrimination circuit 170, only if the image signal 151*a* exceeds the setting of the associated threshold level in the threshold level setter 530 and the image signal 140*a* from the scattered-light detector 130 exceeds the setting of the associated threshold level in the threshold level setter 531. All image signals 151*a*, 140*a*-142*a* are filtered if both of the image signals 151*a*, 140*a* are within the respective threshold levels, that is, unless either of the image signals 151*a*, 140*a* exceeds the associated threshold level.

After steps S651, S653, and S654 are executed, the threshold level setting circuit 160A ends the sequence shown in FIG. 8. The threshold level setting circuit 160A repeatedly executes the successive steps during defect inspection.

Substantially the same advantageous effects as obtained in the first embodiment are also obtainable in the present second embodiment. In addition, since image signal acquisition in accordance with parameter (C2) is possible, a more flexible method of detecting defects can be selected. During image signal acquisition in accordance with parameter (C2), when the scanning direction of light from defects having a specific feature or characteristic, for example, is made clear by the classification/analysis of the defects, estimated defect information on the specific defects can be intensively acquired by attaching, on the basis of a pattern of that scanning direction, importance to the signal(s) detected by the scattered-light detector(s) installed in one specific direction or multiple directions, and acquiring all image signals 151*a*, 140*a*-142*a* only if all those detected signals exceed the associated threshold levels. In this manner, if information on non-intended defects is unnecessary, the amount of data acquired can be reduced even more significantly by acquiring image signals with importance placed on detection results of specific scattered-light detectors, as in acquisition based on parameter (C2).

An example of selecting the image signals 151*a*, 140*a* has been taken in the present embodiment. Signals to be selected, however, can be set arbitrarily. A description has also been given of an example in which the signal (in the present example, image signal 151*a*) that is selected for defect discrimination in accordance with parameter (A2) is a specific image signal of the signals (in the present example, image signals 151*a*, 140*a*) that are selected for defect discrimination in accordance with parameter (C2). However, the present invention is not limited to or by the example, either. Therefore, during image signal acquisition in accordance with parameter (A2), for example, the image signal 140*a* may be used for defect discrimination, and during image signal acquisition in accordance with parameter (C2), the image signals 141*a*, 142*a* may be used for defect discrimination under each parameter. The kind of image signal to be used for defect discrimination is set arbitrarily according to the kind of defect to be detected during inspection based on the desired parameter.

In addition, an example of selecting two image signals, 151*a* and 140*a*, to discriminate defects during image signal acquisition in accordance with parameter (C2) has been described, but three or all (in the second embodiment, four) image signals may be selected.

Furthermore, as in a case of image signal acquisition in accordance with parameter (C2), when a plurality of image signals are set as the signals selected, the present invention may be constructed so as to acquire all image signals if any one of selected multiple images exceeds the associated threshold level, instead of acquiring all image signals if all selected images exceed the respective associated threshold levels. When three or more signals are selected, all image signals are likely to be acquired if more than one of those selected images exceeds the associated threshold level.

Others

In the two embodiments described above, an example in which independent threshold levels are set for each of the image signals 140a-142a from the scattered-light detectors 130-132 and for the image signal 151a formed by arithmetic processing based on the image signals 140a-142a has been described since it is possible to select a mode (parameter B1, B2) for comparing these image signals 151a, 140a-142a with the respective associated threshold levels and acquiring independent image signals. When the mode for acquiring image signals in accordance with parameter (B1) or (B2) is unnecessary, however, there is no need to set threshold levels for individual image signals, and in the mode for acquiring image signals in accordance with image signal acquisition parameter (A1) in the first embodiment or in accordance with parameters (A2) and (C2) in the second embodiment, it suffices just to set only the threshold level(s) associated with the selected signal(s).

In addition, when the mode for acquiring image signals in accordance with parameter (B1) or (B2) is unnecessary, it may be possible to set a common threshold level for each image signal 151a, 140a-142a, instead of providing the signal(s) to be selected, and acquire the image signals 151a, 140a-142a only if any one of these image signals exceeds the common threshold level. In that case, for example, if the threshold level setting circuit 160A in FIG. 7 is used, the same threshold level is set in the threshold level setters 530-533 and all signal acquisition parameter selectors 510-513 are set to ON. Additionally, all image signals 151a, 140a-142a are acquired if either of the image signals 151a, 140a-142a exceeds the associated threshold level (i.e., the common threshold level). If a special setter for setting the common threshold level is provided independently, the threshold level setters 530-533 may be omitted. Furthermore, the number of image signals exceeding the associated threshold levels may be usable for defect discrimination. For example, all image signals 151a, 140a-142a may be acquired only if any two of the image signals 151a, 140a-142a exceed the associated threshold levels or the common threshold level.

Moreover, while an example of using the arithmetic processing circuit 151 to arithmetically process the image signal 151a on the basis of the image signals 140a-142a of the scattered-light detectors 130-132 has been described in the first and second embodiments, arithmetic operations on the image signal 151a are not always necessary if the image signals 140a-142a of the scattered-light detectors 130-132 are detectable. If arithmetic operations on the image signal 151a are not conducted, the arithmetic processing circuit 151, the signal acquisition parameter selector 510, and the threshold level setter 530 are unnecessary and omittable. In this case, under parameter (A1), (A2), or (C2), the defect inspection apparatus can be adapted so that each image signal from the scattered-light detectors 130-132 is acquired if the image signal from either of the scattered-light detectors 130-132 or each image signal from selected multiple scattered-light detectors (all or specific detectors of the selected detectors) exceeds the associated threshold level or the common threshold level. In that case, if a value equivalent to the signal level of the image signal 151a arithmetically obtained in the arithmetic processing circuit 151 is necessary, it suffices just to create a program so that a PC, a reviewing apparatus, an analyzer, or any other processing apparatus provided at a posterior stage separately from, for example, the defect discrimination circuit 170 or the present defect inspection apparatus will conduct data computations based on the image signals 140a-142a.

Although an example in which the present invention is applied to a defect inspection apparatus that irradiates the wafer 1 obliquely with the laser light (inspection light) 31 has been described in the above embodiments, the irradiating direction of the laser light 31 with respect to the wafer 1 is not specifically limited and the invention is applicable to both the defect inspection apparatus adapted to irradiate the wafer 1 obliquely with the laser light 31, and a defect inspection apparatus adapted for vertical irradiation. In addition, although an example in which the present invention is applied to a defect inspection apparatus that uses dark-field data to detect defects has been described, the invention can also be applied if one inspection apparatus has a plurality of detectors in other cases.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. An inspection apparatus comprising:
   an irradiation system which irradiates a substrate with light;
   a plurality of detectors arranged in a plurality of directions relative to said substrate, each detector configured to detect light from said substrate and generate a plurality of signals;
   a plurality of channels, each channel coupled to a respective one of said detectors and configured to receive a signal from the respective detector; and
   an electronic filter for comparing one of said signals against a threshold, wherein:
   said electronic filter is configured to filter out said one signal and filter out said other signals if said one signal is less than the threshold, or said electronic filter is configured to pass said one signal and pass said other signals if said one signal exceeds the threshold.

2. An inspection method comprising steps of:
   irradiating a substrate with light by way of an irradiation system;
   detecting light from said substrate by a plurality of detectors arranged in a plurality of directions relative to said substrate and generating a plurality of signals;
   receiving a signal at a plurality of channels, each channel coupled to a respective one of said detectors and configured to receive a signal from the respective detector;
   comparing, by way of an electronic filter, one of said signals against a threshold;
   filtering out said one signal and said other signals by said electronic filter if said one signal is less than the threshold; or passing said one signal and said other signals by said electronic filter if said one signal exceeds the threshold.

* * * * *